(12) United States Patent
Zhang

(10) Patent No.: US 8,754,256 B2
(45) Date of Patent: *Jun. 17, 2014

(54) PROCESS FOR PREPARATION OF L-ARGININE α-KETOGLUTARATE 1:1 AND 2:1

(75) Inventor: Guoji Zhang, Tianjin (CN)

(73) Assignee: Tianjin Tiancheng Pharmaceutical Co., Ltd. (China), Tianjin (CN)

( * ) Notice: Subject to any disclaimer, the term of this patent is extended or adjusted under 35 U.S.C. 154(b) by 471 days.

This patent is subject to a terminal disclaimer.

(21) Appl. No.: 12/925,125

(22) Filed: Oct. 13, 2010

(65) Prior Publication Data

US 2012/0095260 A1    Apr. 19, 2012

(51) Int. Cl.
    *C07C 229/26*    (2006.01)
(52) U.S. Cl.
    USPC .......................................................... 562/560
(58) Field of Classification Search
    CPC ............................. C07C 279/14; C07C 59/347
    See application file for complete search history.

(56) References Cited

U.S. PATENT DOCUMENTS 3,723,248 A * 3/1973 Tanaka et al. .................. 435/143
4,296,127 A * 10/1981 Walser .......................... 514/564

FOREIGN PATENT DOCUMENTS

ES    392277 A1 *  1/1974
GB    1199547    *  7/1970

OTHER PUBLICATIONS

Timmler et al, Angewandte Chemie, alpha,alpha-Dichlorglutarsäureester, 72(24), p. 1001, with CAS Abstract.*

* cited by examiner

*Primary Examiner* — Paul A Zucker
(74) *Attorney, Agent, or Firm* — Raymond Y. Chan; David and Raymond Patent Firm

(57) ABSTRACT

A process for preparation of α-ketoglutaric acid, L-arginine α-ketoglutarate 1:1 and 2:1 includes the following steps. Provide a α-ketoglutaratic acid aqueous solution at an adjusted concentration. Add one equivalent mole of solid L-arginine to the α-ketoglutaratic acid aqueous solution. Stir and allow reaction under a controlled temperature. Obtain a resulting L-arginine α-ketoglutarate 1:1 solution with a pH of approximately 3~4 or L-arginine α-ketoglutarate 2:1 solution with a pH of approximately 6.5~7. Obtain a final product of L-arginine α-ketoglutarate 1:1 or 2:1 through spay drying. The yield of the final product is approximately 94% for L-arginine α-ketoglutarate 1:1 and 97% for L-arginine α-ketoglutarate 2:1 through the process. Large amount of solvents is eliminated and reaction time is shortened but the yield is increased, hence realizing mass production through reactor in a cost and time effective manner.

11 Claims, 3 Drawing Sheets

PROCESS FOR PREPARATION OF L-ARGININE α-KETOGLUTARATE 1:1 AND 2:1

BACKGROUND OF THE PRESENT INVENTION

1. Field of Invention

The present invention relates to a process of preparation of L-Arginine ketoglutarate 1:1 and 2:1, and more particularly to a process of preparation of L-Arginine ketoglutarate 1:1 and 2:1 which employs solid L-Arginine as raw materials directly to react with α-Ketoglutaric acid such that mass production of a high yield and low cost end product is realized.

2. Description of Related Arts

L-arginine α-ketoglutarate 1:1 and 2:1 are widely used as sports nutrition ingredients. However, conventional method of preparation of L-arginine α-ketoglutarate 1:1 and 2:1 are complicated, time consuming and costly which are not suitable for industrialization. In particular, the conventional method makes use of L-arginine solution and large amount of organic solvents for the reactions, and obtains the final products of L-arginine α-ketoglutarate 1:1 and 2:1 through crystallization. The high level of complexity, the large amount of organic solvents required, the high production cost and the high production time required have make it difficult for mass production of L-arginine α-ketoglutarate 1:1 and 2:1 and industrialization.

SUMMARY OF THE PRESENT INVENTION

The invention is advantageous in that it provides a method of preparation of L-arginine α-ketoglutarate 1:1 which is cost effective and suitable for mass production.

Another advantage of the invention is to provide a method of preparation of L-arginine α-ketoglutarate 1:1 which does not require the use of a large amount of solvents throughout the process.

Another advantage of the invention is to provide a method of preparation of L-arginine α-ketoglutarate 1:1 through which a shorten period of production time is required to obtain a higher yield of final products.

Another advantage of the invention is to provide a method of preparation of L-arginine α-ketoglutarate 2:1 which is cost effective and suitable for mass production.

Another advantage of the invention is to provide a method of preparation of L-arginine α-ketoglutarate 2:1 which does not require the use of a large amount of solvents throughout the process.

Another advantage of the invention is to provide a method of preparation of L-arginine α-ketoglutarate 2:1 through which a shortened period of production time is required to obtain a higher yield of final products.

Additional advantages and features of the invention will become apparent from the description which follows, and may be realized by means of the instrumentalities and combinations particular point out in the appended claims.

According to the present invention, the foregoing and other objects and advantages are attained by a method of preparation of L-arginine α-ketoglutarate 1:1 through a reactor comprising the steps of:

(i) reacting methyl dichloroacetate and acrylic acid methyl ester with sodium methoxide to obtain dimethyl 2,2-dichloroglutarate;

(ii) reacting dimethyl 2,2-dichloroglutarate hydroxide solution to obtain a crude α-ketoglutaratic acid aqueous solution;

(iii) purifying the crude α-ketoglutaratic acid aqueous solution to obtain a purified α-ketoglutaratic acid aqueous solution, and providing the purified α-ketoglutaratic acid aqueous solution in the reactor;

(iv) adjusting a concentration of the purified α-ketoglutaratic acid aqueous solution by adding water into the reactor;

(v) adding a quantity of solid L-arginine to the purified α-ketoglutaratic acid aqueous solution, wherein the quantity of the solid L-arginine is equals to one equivalent mole of the purified α-ketoglutaratic acid aqueous solution;

(v') stirring a mixture of solid L-arginine and the purified α-ketoglutaratic acid aqueous solution through the reactor;

(v'') setting a controlled temperature of the reactor such that the solid L-arginine dissolves and reacts with the purified α-ketoglutaratic acid aqueous solution in the reactor at the controlled temperature for a controlled period of time;

(vi) obtaining a resulting L-arginine α-ketoglutarate 1:1 solution from step (v''), wherein a pH of the resulting L-arginine α-ketoglutarate 1:1 solution is approximately 3~4; and (vii) obtaining a final product of L-arginine α-ketoglutarate 1:1 from step (vi) through spay drying, wherein a yield of the final product is approximately 94%.

In accordance with another aspect of the invention, the present invention provides a method of preparation of L-arginine α-ketoglutarate 2:1 through a reactor comprising the steps of:

(i) reacting methyl dichloroacetate and acrylic acid methyl ester with sodium methoxide to obtain dimethyl 2,2-dichloroglutarate;

(ii) reacting dimethyl 2,2-dichloroglutarate hydroxide solution to obtain a crude α-ketoglutaratic acid aqueous solution;

(iii) purifying the crude α-ketoglutaratic acid aqueous solution to obtain a purified α-ketoglutaratic acid aqueous solution, and providing the purified α-ketoglutaratic acid aqueous solution in the reactor;

(iv) adjusting a concentration of the purified α-ketoglutaratic acid aqueous solution by adding water into the reactor;

(v) adding a quantity of solid L-arginine to the purified α-ketoglutaratic acid aqueous solution, wherein the quantity of the solid L-arginine is equals to two equivalent mole of the purified α-ketoglutaratic acid aqueous solution;

(v') stirring a mixture of solid L-arginine and the purified α-ketoglutaratic acid aqueous solution through the reactor;

(v'') setting a controlled temperature of the reactor such that the solid L-arginine dissolves and reacts with the purified α-ketoglutaratic acid aqueous solution in the reactor at the controlled temperature for a controlled period of time;

(vi) obtaining a resulting L-arginine α-ketoglutarate 2:1 solution from step (v''), wherein a pH of the resulting L-arginine α-ketoglutarate 2:1 solution is approximately 6.5~7; and (vii) obtaining a final product of L-arginine α-ketoglutarate 2:1 from step (vi) through spay drying, wherein a yield of the final product is approximately 97%.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

Figure 1:
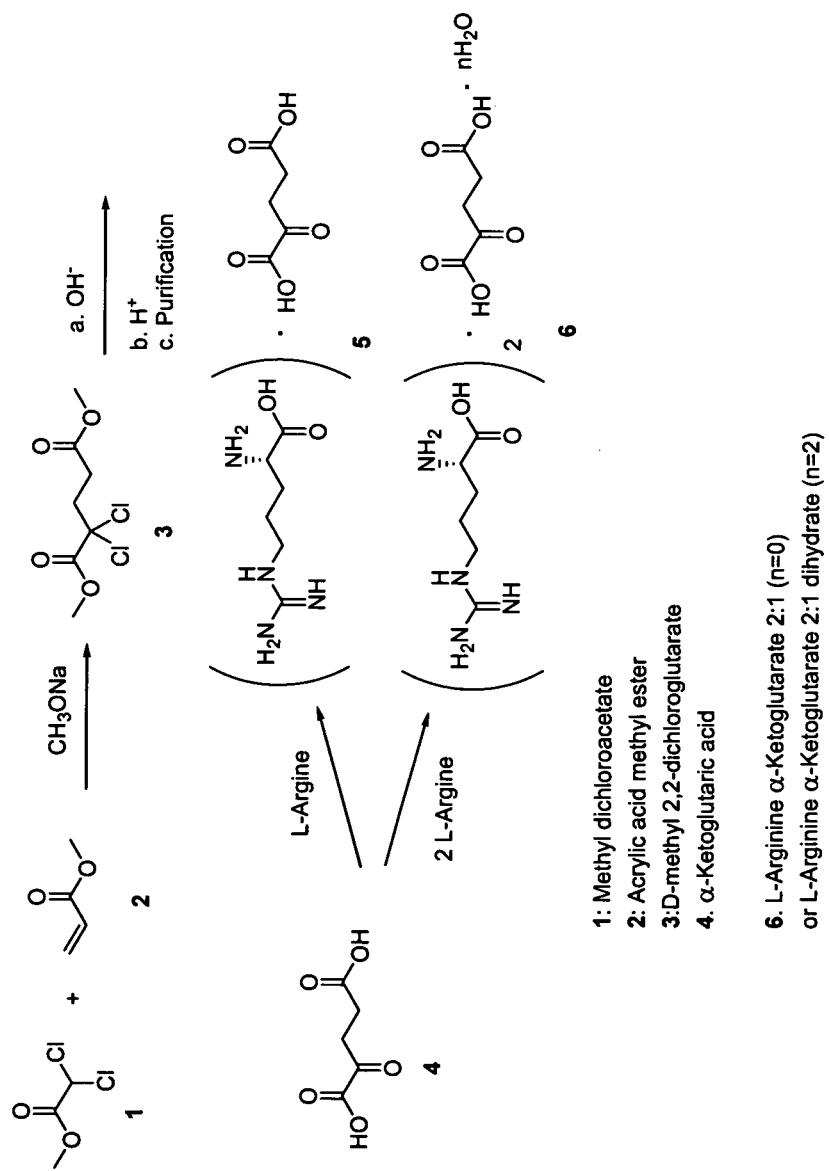
FIG. 1 is a schematic illustration of a method of preparation of L-arginine α-ketoglutarate 1:1 and 2:1 according to a preferred embodiment of the present invention.
Figure 2:
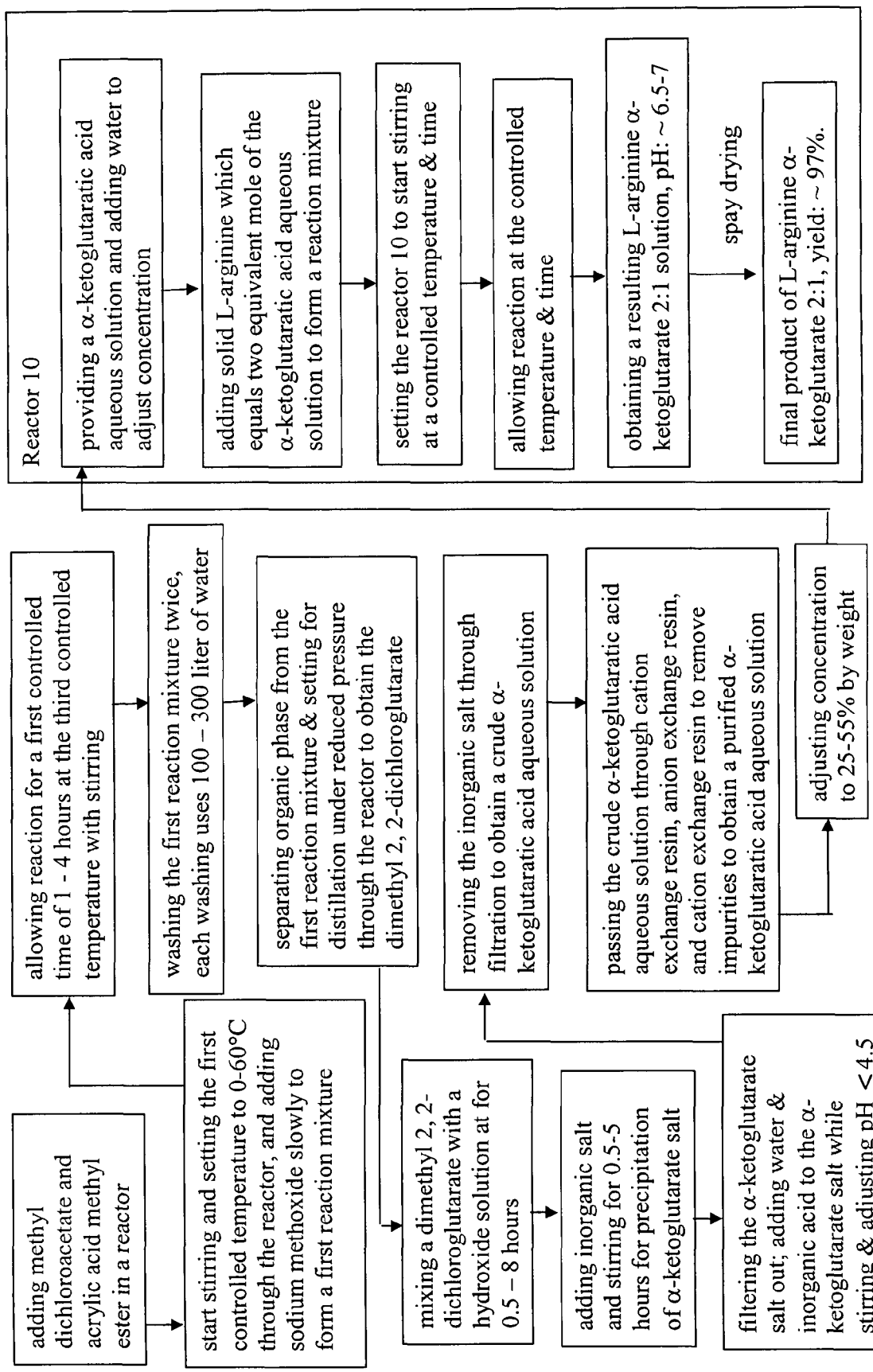
FIG. 2 is a block diagram of a method of preparation of L-arginine α-ketoglutarate 1:1 according to the above preferred embodiment of the present invention.
Figure 3:
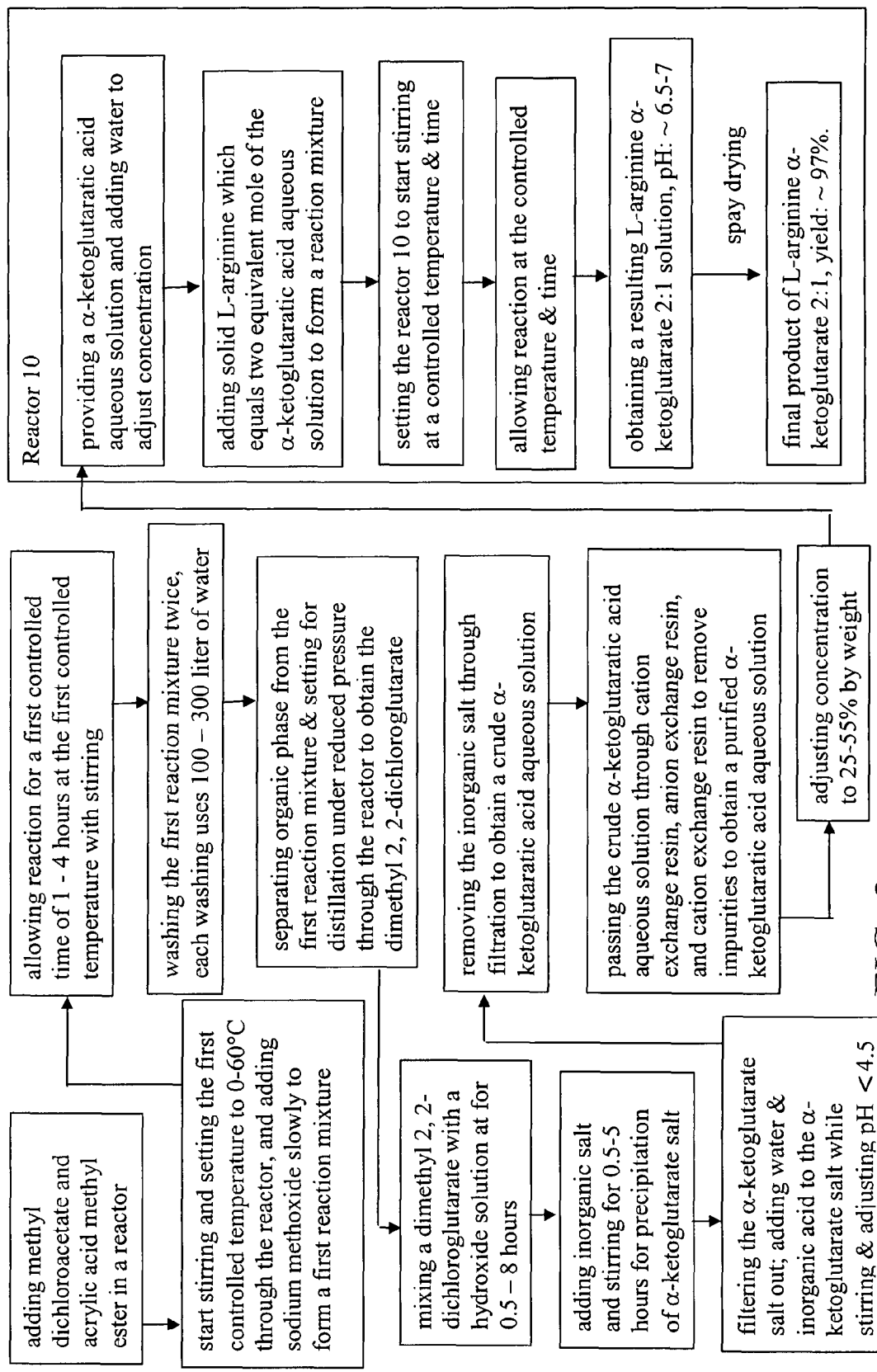
FIG. 3 is a block diagram of a method of preparation of L-arginine α-ketoglutarate 2:1 according to the above preferred embodiment of the present invention.

Referring to FIGS. 1 to 3 of the drawings, a method of preparation of L-arginine α-ketoglutarate 1:1 and 2:1 according to a preferred embodiment of the present invention comprises the steps of:

(i) reacting methyl dichloroacetate and acrylic acid methyl ester with sodium methoxide to obtain dimethyl 2,2-dichloroglutarate;

(ii) reacting dimethyl 2,2-dichloroglutarate with a hydroxide solution to obtain a crude α-ketoglutaratic acid aqueous solution;

(iii) purifying the crude α-ketoglutaratic acid aqueous solution to obtain a purified α-ketoglutaratic acid aqueous solution;

(iv) adjusting a concentration of the purified α-ketoglutaratic acid aqueous solution by adding water;

(v) adding a quantity of solid L-arginine to the purified α-ketoglutaratic acid aqueous solution, wherein the quantity of the solid L-arginine is equals to one equivalent mole of the purified α-ketoglutaratic acid aqueous solution for producing L-arginine α-ketoglutarate 1:1, wherein the quantity of the solid L-arginine is equals to two equivalent moles of the purified α-ketoglutaratic acid aqueous solution for producing L-arginine α-ketoglutarate 2:1;

(vi) obtaining a resulting L-arginine α-ketoglutarate 1:1 solution or 2:1 solution from step (v), wherein a pH of the resulting L-arginine α-ketoglutarate 1:1 solution is approximately 3~4, wherein a pH of the resulting L-arginine α-ketoglutarate 2:1 solution is approximately 6.5~7; and (vii) obtaining a final product of L-arginine α-ketoglutarate 1:1 or 2:1 from step (vi) through spray drying, wherein a yield of the final product of L-arginine α-ketoglutarate 1:1 is approximately 94%, wherein a yield of the final product of L-arginine α-ketoglutarate 2:1 is approximately 97%.

In particular, referring to FIGS. 1 and 2 of the drawings, a method of preparation of L-arginine α-ketoglutarate 1:1 according to a preferred embodiment of the present invention comprises the steps of:

(i) reacting methyl dichloroacetate and acrylic acid methyl ester with sodium methoxide to obtain Dimethyl 2,2-dichloroglutarate;

(ii) reacting dimethyl 2,2-dichloroglutarate with a hydroxide solution to obtain a crude α-ketoglutaratic acid aqueous solution;

(iii) purifying the crude α-ketoglutaratic acid aqueous solution to obtain a purified α-ketoglutaratic acid aqueous solution;

(iv) adjusting a concentration of the purified α-ketoglutaratic acid aqueous solution by adding water;

(v) adding a quantity of solid L-arginine to the purified α-ketoglutaratic acid aqueous solution, wherein the quantity of the solid L-arginine is equals to one equivalent mole of the purified α-ketoglutaratic acid aqueous solution;

(vi) obtaining a resulting L-arginine α-ketoglutarate 1:1 solution from step (v), wherein a pH of the resulting L-arginine α-ketoglutarate 1:1 solution is approximately 3~4; and (vii) obtaining a final product of L-arginine α-ketoglutarate 1:1 from step (vi) through spray drying, wherein a yield of the final product is approximately 94%.

In particular, referring to FIGS. 1 and 3 of the drawings, a method of preparation of L-arginine α-ketoglutarate 2:1 according to a preferred embodiment of the present invention comprises the steps of:

(i) reacting methyl dichloroacetate and acrylic acid methyl ester with sodium methoxide to obtain Dimethyl 2,2-dichloroglutarate;

(ii) reacting dimethyl 2,2-dichloroglutarate with a hydroxide solution to obtain a crude α-ketoglutaratic acid aqueous solution;

(iii) purifying the crude α-ketoglutaratic acid aqueous solution to obtain a purified α-ketoglutaratic acid aqueous solution;

(iv) adjusting a concentration of the purified α-ketoglutaratic acid aqueous solution by adding water;

(v) adding a quantity of solid L-arginine to the purified α-ketoglutaratic acid aqueous solution, wherein the quantity of the solid L-arginine is equals to two equivalent mole of the purified α-ketoglutaratic acid aqueous solution;

(vi) obtaining a resulting L-arginine α-ketoglutarate 2:1 solution from step (v), wherein a pH of the resulting L-arginine α-ketoglutarate 2:1 solution is approximately 6.5~7; and (vii) obtaining a final product of L-arginine α-ketoglutarate 2:1 from step (vi) through spray drying, wherein a yield of the final product is approximately 97%.

Referring to FIGS. 1 to 3 of the drawings, preferably, the preparation of dimethyl 2,2-dichloroglutarate is further described as follows:

In a 3000 liter reactor, methyl dichloroacetate and acrylic acid methyl ester are added. The stirring is controlled to start and a first controlled temperature is adjusted to 0-60° C. Then, sodium methoxide is added slowly to form a first reaction mixture. After the sodium methoxide is added, the first reaction mixture is stirred at the first controlled temperature for 1-4 hours. Subsequently, 100-300 liter of water is added to wash the first reaction mixture. The first reaction mixture is washed with water twice. The organic phase is then separated and distillation under reduced pressure is set to obtain dimethyl 2, 2-dichloroglutarate.

In other words, the step (i) is carried out through the following steps:

(i.1) adding methyl dichloroacetate and acrylic acid methyl ester in a reactor;

(i.2) start stirring and setting a first controlled temperature of 0-60° C. through the reactor;

(i.3) adding sodium methoxide slowly to form a first reaction mixture;

(i.4) allowing reaction for 1-4 hours in the reactor at the first controlled temperature with stirring;

(i.5) washing the first reaction mixture after step (i.4) twice, wherein, preferably, 100-300 liter of water is added for each washing; and (i.6) separating organic phase from the first reaction mixture in step (i.5), and setting for distillation under reduced pressure through the reactor to obtain dimethyl 2,2-dichloroglutarate.

It is worth mentioning that no organic solvent is used in the preparation of dimethyl 2,2-dichloroglutarate, as illustrated in the above process.

Preferably, the preparation of α-ketoglutaratic acid is further described as follows:

Dimethyl 2, 2-dichloroglutarate 3 obtained from the above method is mixed with a hydroxide solution at a second controlled temperature for 0.5-8 hours to form a second mixture.

Inorganic salt is added to the second mixture and is stirred for 0.5-5 hours to form a large amount precipitate. The second mixture is then filtered to obtain α-ketoglutarate salt, which is stirred with water and inorganic acid to pH <4.5. The inorganic salt is then removed through filtration to obtain a crude α-ketoglutaratic acid aqueous solution.

In other words, the step (ii) is carried out through the following steps:

(ii.1) mixing the dimethyl 2,2-dichloroglutarate obtained from step (i) with a hydroxide solution at a second controlled temperature for 0.5-8 hours to form a second mixture;

(ii.2) adding inorganic salt to the second mixture and stirring for 0.5-5 hours for precipitation of α-ketoglutarate salt;

(ii.3) filtering the α-ketoglutarate salt out; adding water and inorganic acid to the α-ketoglutarate salt while stirring and adjusting a pH to pH <4.5; and (ii.4) removing the inorganic salt through filtration to obtain the crude α-ketoglutaratic acid aqueous solution.

Preferably, the purification of α-ketoglutaratic acid is further described as follows:

The crude α-ketoglutaratic acid aqueous solution obtained from the above process is passed through cation exchange resin, anion exchange resin, and cation exchange resin to remove impurities. Then, the aqueous solution obtained is concentrated to 25-55% by weight, which is to be used as the starting material for preparation of L-arginine α-ketoglutarate 1:1 and 2:1.

In other words, the step (iii) is carried out through the following steps:

(iii.1) passing the crude α-ketoglutaratic acid aqueous solution through cation exchange resin, anion exchange resin, and cation exchange resin to remove impurities to obtain a purified α-ketoglutaratic acid aqueous solution; and (iii.2) adjusting a concentration of the purified α-ketoglutaratic acid aqueous solution to 25-55% by weight.

The overall yield for steps (i) to (iii) from the above process is 75%. In step (iii.1), both cation and anion exchange resins are used to remove impurities effectively.

Preferably, referring to FIG. 2 of the drawings, the preparation of L-arginine α-ketoglutarate 1:1 is further described as follows:

In a reactor, the purified and concentrated α-ketoglutaratic acid solution is added followed by water to adjust to a certain concentration. One equivalent mole of solid L-arginine is added while the reaction mixture is being stirred. The temperature is controlled to dissolve all solid and form pH 3-4 L-arginine α-ketoglutarate 1:1 solution. The final product is obtained directly via spray drying with a yield of 94%.

In other words, the preparation of L-arginine α-ketoglutarate 1:1 from α-ketoglutaratic acid solution is carried out through the following steps:

(iv) setting a concentration of the purified α-ketoglutaratic acid aqueous solution by adding water;

(v) adding a quantity of solid L-arginine to the purified α-ketoglutaratic acid aqueous solution, wherein the quantity of the solid L-arginine is equals to one equivalent mole of the purified α-ketoglutaratic acid aqueous solution;

(vi) obtaining a resulting L-arginine α-ketoglutarate 1:1 solution from step (v), wherein a pH of the resulting L-arginine α-ketoglutarate 1:1 solution is approximately 3~4; and (vii) obtaining a final product of L-arginine α-ketoglutarate 1:1 from step (vi) through spay drying, wherein a yield of the final product is approximately 94%.

Preferably, referring to FIG. 3 of the drawings, the preparation of L-arginine α-ketoglutarate 2:1 is further described as follows:

In a reactor, the purified and concentrated α-ketoglutaratic acid solution is added followed by water to adjust to a certain concentration. Two equivalent mole of solid L-arginine is added while the reaction mixture is being stirred. The temperature is controlled to dissolve all solid and form pH 6.5-7 L-arginine α-ketoglutarate 2:1 solution. The final product is obtained directly via spray drying with a yield of 97%.

In other words, the preparation of L-arginine α-ketoglutarate 2:1 from α-ketoglutaratic acid solution is carried out through the following steps:

(iv) setting a concentration of the purified α-ketoglutaratic acid aqueous solution by adding water;

(v) adding a quantity of solid L-arginine to the purified α-ketoglutaratic acid aqueous solution, wherein the quantity of the solid L-arginine is equals to two equivalent mole of the purified α-ketoglutaratic acid aqueous solution;

(vi) obtaining a resulting L-arginine α-ketoglutarate 2:1 solution from step (v), wherein a pH of the resulting L-arginine α-ketoglutarate 2:1 solution is approximately 6.5~7; and (vii) obtaining a final product of L-arginine α-ketoglutarate 2:1 from step (vi) through spay drying, wherein a yield of the final product is approximately 97%.

It is worth mentioning that solid L-arginine is added directly to the α-ketoglutaratic acid solution to eliminate the need to prepare L-arginine solution. The product solution is spray dried directly to obtain the final product in dry product powder. Compared to the conventional processes, the method of preparation of the present invention eliminates the use of a large amount of organic solvents and reduces the production time and cost.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method of preparing L-arginine α-ketoglutarate 1:1, comprising the steps of:

(a) providing a α-ketoglutaric acid aqueous solution and adding water to adjust concentration of the α-ketoglutaric acid aqueous solution, wherein the α-ketoglutaric acid aqueous solution is prepared and purified by the steps of:

(a.1) mixing a dimethyl 2, 2-dichloroglutarate with a hydroxide solution at a second controlled temperature for 0.5-8 hours to form a first mixture, wherein the dimethyl 2, 2-dichloroglutarate is prepared by the steps of:

(a.1.1) stirring methyl dichloroacetate and acrylic acid methyl ester at a first controlled temperature of 0-60° C.;

(a.1.2) adding sodium methoxide slowly to form a first reaction mixture;

(a.1.3) allowing reaction for a first controlled time of 1-4 hours at the first controlled temperature with stirring;

(a.1.4) washing the first reaction mixture after step (a.1.3) twice, wherein 100-300 liter of water is added for each of the washing; and (a.1.5) separating organic phase from the first reaction mixture in step (a.1.4), and obtain the dimethyl 2, 2-dichloroglutarate through distillation under reduced pressure;

(a.2) adding inorganic salt to the first mixture and stirring for 0.5-5 hours for precipitation of α-ketoglutarate salt;

(a.3) filtering the α-ketoglutarate salt out, and adding water and inorganic acid to the α-ketoglutarate salt while stirring and adjusting pH thereof <4.5;

(a.4) removing the inorganic salt through filtration to obtain a crude α-ketoglutaric acid aqueous solution; and (a.5) removing impurities from the crude α-ketoglutaric acid aqueous solution by passing the crude α-ketoglutaric acid aqueous solution through one of cation exchange resin and anion exchange resin to obtain a purified α-ketoglutaric acid aqueous solution;

(b) adding solid L-arginine as raw materials to directly react with the purified α-ketoglutaric acid aqueous solution to form a reaction mixture, (c) allowing reaction of the reaction mixture at a first controlled temperature for a first controlled period of time;

(e) obtaining a resulting L-arginine α-ketoglutarate 1:1 solution from step (d), wherein pH of the resulting L-arginine α-ketoglutarate 1:1 solution is approximately 3 to 4 when preparing L-arginine α-ketoglutarate 1:1; and (f) obtaining a final product of L-arginine α-ketoglutarate 1:1 from step (e) through spray drying.

2. The method as recited in claim 1 wherein, in the step (b), quantity of the solid L-arginine equals to one equivalent mole of the α-ketoglutaric acid aqueous solution when preparing L-arginine α-ketoglutarate 1:1.

3. The method as recited in claim 1 wherein, in the step (a), concentration of the α-ketoglutaric acid aqueous solution is 25-55% by weight.

4. The method as recited in claim 1 wherein the step (a), after step (a.5), further comprises a step of:
(a.6) adjusting concentration of the purified α-ketoglutaric acid aqueous solution to 25-55% by weight.

5. The method, as recited in claim 1, wherein overall yield of the purified α-ketoglutaric acid aqueous solution in the step (a) prepared from the methyl dichloroacetate and the acrylic acid methyl ester through the steps (a.1.1) to (a.1.5), and the steps (a.1) to (a.6) is 75%.

6. A method of preparing L-arginine α-ketoglutarate 1:1 through a reactor for mass production of L-arginine α-ketoglutarate 1:1, comprising the steps of:
(a) providing a α-ketoglutaric acid aqueous solution in the reactor, and adding water to adjust concentration of the α-ketoglutaric acid aqueous solution, wherein the α-ketoglutaric acid aqueous solution is prepared and purified by the steps of:
(a.1) mixing a dimethyl 2, 2-dichloroglutarate with a hydroxide solution at a second controlled temperature for 0.5-8 hours to form a first mixture, wherein the dimethyl 2, 2-dichloroglutarate is prepared by the steps of:
(a.1.1) adding methyl dichloroacetate and acrylic acid methyl ester in the reactor;

(a.1.2) start stirring and setting a first controlled temperature to 0-60° C. through the reactor, and adding sodium methoxide slowly to form a first reaction mixture;

(a.1.3) allowing reaction for a first controlled time of 1-4 hours at the first controlled temperature with stirring;

(a.1.4) washing the first reaction mixture after step (a.1.3') twice, wherein 100-300 liter of water is added for each of the washing; and (a.1.5) separating organic phase from the first reaction mixture in step (a.1.4'), and setting for distillation under reduced pressure through the reactor to obtain the dimethyl 2, 2-dichloroglutarate;

(a.2) adding inorganic salt to the first mixture and stirring for 0.5-5 hours for precipitation of α-ketoglutarate salt;

(a.3) filtering the α-ketoglutarate salt out, and adding water and inorganic acid to the α-ketoglutarate salt while stirring and adjusting pH thereof <4.5;

(a.4) removing the inorganic salt through filtration to obtain a crude α-ketoglutaric acid aqueous solution; and (a.5) removing impurities from the crude α-ketoglutaric acid aqueous solution by passing the crude α-ketoglutaric acid aqueous solution through one of cation exchange resin and anion exchange resin to obtain a purified α-ketoglutaric acid aqueous solution;

(b) adding solid L-arginine as raw materials to directly react with the purified α-ketoglutaric acid aqueous solution to form a reaction mixture;

(c) setting the reactor to start stirring and to a controlled temperature for a controlled period of time such that the reaction mixture of solid L-arginine and the α-ketoglutaric acid aqueous solution is stirred in the reactor under the controlled temperature;

(d) allowing reaction of the reaction mixture at the controlled temperature for the controlled period of time in the reactor;

(e) obtaining a resulting L-arginine α-ketoglutarate 1:1 solution from step (d'), wherein pH of the resulting L-arginine α-ketoglutarate 1:1 solution is approximately 3~4; and (f) obtaining a final product of L-arginine α-ketoglutarate 1:1 from step (e') through spray drying.

7. The method as recited in claim 6 wherein, in the step (b), quantity of the solid L-arginine equal to one equivalent mole of the α-ketoglutaric acid aqueous solution.

8. The method as recited in claim 6 wherein, in the step (f), yield of the final product is approximately 94%.

9. The method as recited in claim 6 wherein, in the step (a), concentration of the α-ketoglutaric acid aqueous solution is 25-55% by weight.

10. The method as recited in claim 6, wherein the step (a), after step (a.5), further comprises a step of:
(a.6) adjusting concentration of the purified α-ketoglutaric acid aqueous solution to 25-55% by weight.

11. The method, as recited in claim 6, wherein overall yield of the purified α-ketoglutaric acid aqueous solution in the step (a) prepared from the methyl dichloroacetate and the acrylic acid methyl ester through the steps (a.1.1') to (a.1.5'), and the steps (a.1) to (a.6) is 75%.

* * * * *